US00PP11747P2

(12) United States Plant Patent
Sanford et al.

(10) Patent No.: US PP11,747 P2
(45) Date of Patent: Jan. 23, 2001

(54) RED RASPBERRY PLANT NAMED 'PRELUDE'

(75) Inventors: John C. Sanford, Geneva; Kevin E. Maloney, Phelps; Jack E. Reich, Geneva, all of NY (US); Donald K. Ourecky, Fort Lauderdale, FL (US)

(73) Assignee: Cornell Research Foundation, Inc., Ithaca, NY (US)

( * ) Notice: Under 35 U.S.C. 154(b), the term of this patent shall be extended for 0 days.

(21) Appl. No.: 09/166,854

(22) Filed: Oct. 6, 1998

(51) Int. Cl.[7] ..... A01H 5/00
(52) U.S. Cl. ..... Plt./204
(58) Field of Search ..... Plt./204

(56) References Cited

U.S. PATENT DOCUMENTS

P.P. 6,597 * 2/1989 Keep ..... Plt./204
P.P. 7,436 * 2/1991 Ackerman ..... Plt./204

OTHER PUBLICATIONS

Program and Abstracts Seventh International Rubus–Ribes Symposium Australia and New Zealand, Jan. 9–16, 1998, title page and p. 7.

Proceedings 1998 Pennsylvania Vegetable Conference and Trade Show, Hershey, PA, presentation Jan. 28, 1998, title page, pp. 3 and 45.

1998 New York State Vegetable Conference and Berry Growers Meeting Feb. 10–12, Proceedings, title pages, table of contents, pp. 7, 8, 9.

New York Berry Grower, Apr. 1998, pp. 1 and 7.

New York Berry Grower, Dec. 1997, pp. 1, 10 and 11.

News Releases by Department of Communications, NYSAES, Geneva, New York, on Feb. 10, 1998, pp. 1 and 4.

Cornell University Station News, vol. LXXIX, No. 6, Feb. 13–20, 1998, NYSAES, Geneva, New York, p. 1.

CALS News (monthly newsletter of College of Agriculture and Life Sciences) of Cornell University, vol. 4–6, Mar. 1998, pp. 1 and 2.

New York's Food and Life Sciences Bulletin, No. 153, Jan. 1998.

* cited by examiner

*Primary Examiner*—Bruce R. Campell
*Assistant Examiner*—Wendy A. Baker

(57) ABSTRACT

A new and distinct cultivar of red raspberry plant named 'Prelude' is a very early maturing summer red raspberry cultivar available for production in the East Coast and Great Lakes regions, peaking in production in late June and very early July.

6 Drawing Sheets

The invention was made in part with Federal formula funds pursuant to the Hatch Act and was part of Project 632-496. The United States Government has certain rights in the invention.

BACKGROUND OF THE INVENTION

Early maturing cultivars in the East Coast and Great Lakes regions mature only about 10–15% of their crop by July 10. Providing a red raspberry plant that matures a high percentage of fruit in late June and very early July in the East Coast and Great Lakes regions would have the benefit of increasing the length of the harvest season in these regions.

SUMMARY OF THE INVENTION

This invention relates to a new and distinct cultivar of red raspberry plant that matures early in the East Coast and Great Lakes regions, named 'Prelude.' It is the earliest maturing summer red raspberry cultivar available for production in the East Coast and Great Lakes regions known to us, peaking in production in late June and very early July. The 'Prelude' plant also bears fruit on primocanes in the fall. The 'Prelude' plant has the ability to produce a competitive summer crop, in terms of fruit quality and yield, and also produce a fall crop. 'Prelude' plants are winter hardy in zone 5 and are vigorous. 'Prelude' canes are vigorous and sucker freely. 'Prelude' canes are of average height compared to other early cultivars. 'Prelude' canes have sparse but noticeable spines. 'Prelude' canes differ from those of another early maturing cultivar, 'Killarney', (unpatented) in spine density on the dormant cane base and in dormant cane base color and in spine diameter and density on dormant cane tip and in dormant cane tip color. 'Prelude' fruit are round-conic in shape and are coherent and uniform. Fruit are high quality and firm. Fruit are positioned openly with good placement and are very easy to harvest. Average fruit size and yield are similar to other East Coast and Great Lakes early varieties.

The photographs of FIGS. 6–11 are magnified and made under artificial lighting, i.e., said photographs were made using a dissecting microscope for magnification and artificial lighting in a procedure ordinarily carried out under artificial lighting.

DETAILED DESCRIPTION

The 'Prelude' plant is a new red raspberry plant developed by Cornell University at the New York State Agricultural Experiment Station in Geneva, N.Y. The 'Prelude' cultivar originated from a cross of NY817(unpatented) ['Hilton' (unpatented)×'NY60' (unpatented) ('Durham' (unpatented)×'September'(unpatented)]×'Hilton.' The original cross was made in 1971 and 'Prelude' was the only selection made from the 141 progeny of the seedling population. The 'Prelude' plant was tested at six sites in Geneva, N.Y. 'Prelude' has been asexually propagated utilizing tissue culture techniques, specifically, meristem culture and multiplication with the original explant material being meristems excised from dormant buds in primocane leaf axils, and root sucker propagation at Nourse Farms, Inc., 41 River Road, South Deerfield, Mass., 01373. Scientists and licensed evaluators have tested several thousand propagules. These plants have remained stable and true to type. The 'Prelude' plant was previously known and tested as NY1009.

Figure 1:
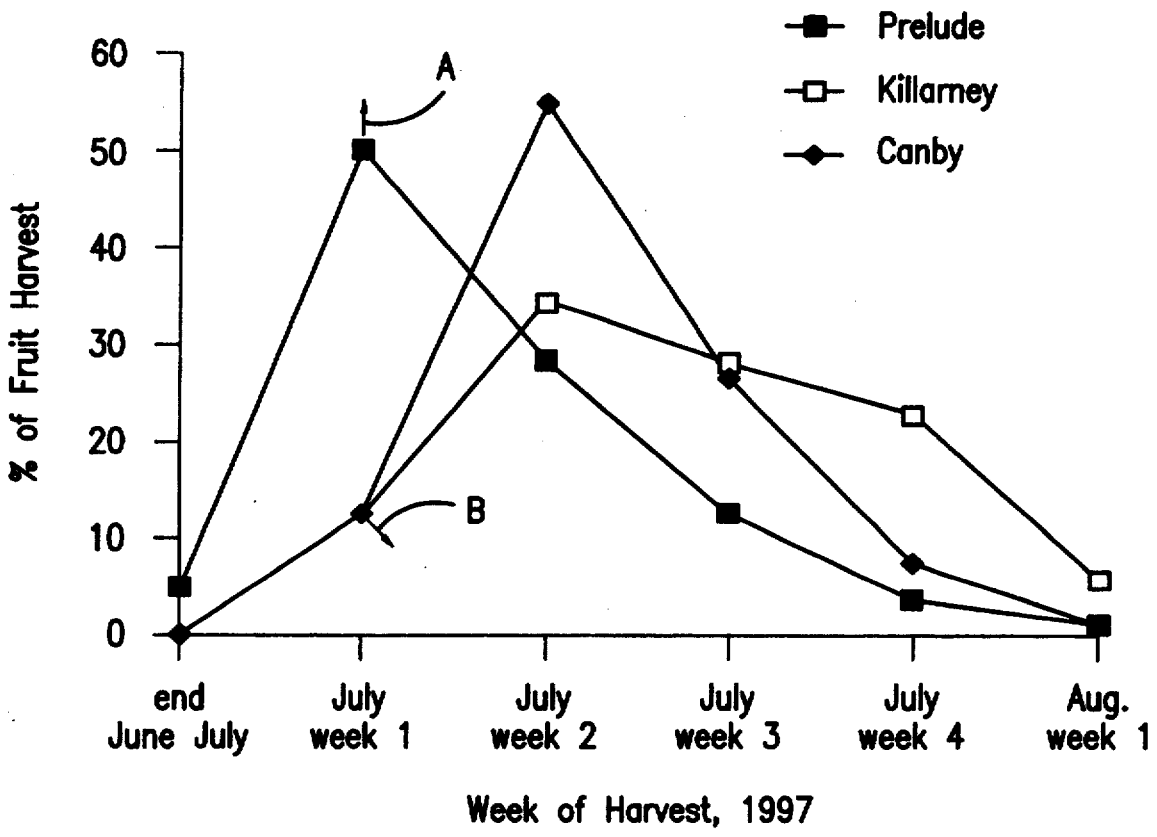
FIG. 1 depicts a graph showing time and amount of fruit maturing for 'Prelude' and two other early maturing red raspberry cultivars adapted to the East Coast and Great Lakes regions.

FIG. 1 compares the fruit maturities of 'Prelude,' 'Killarney' and 'Canby' (unpatented) red raspberry plant cultivars for summer harvesting in 1997. 'Killarney' and 'Canby' are standard early red raspberry cultivars for the East Coast and Great Lakes regions. FIG. 1 shows that 'Prelude' red raspberry plants matured 55% of their total crop in Geneva, N.Y. by July 11 as denoted by reference letter A. FIG. 1 shows that 'Killarney' and 'Canby' red raspberry plants matured 12% of their total crop in Geneva, N.Y. by July 11 as denoted by reference letter B. The average date of first harvest for the 'Prelude' red raspberry plant in Geneva, N.Y. from 1993 to 1997 was July 1, ranging from June 26 to July 5. From 1994 to 1997, the 'Prelude' red raspberry plant on average matured 50% of its fruit by July 10, compared with 13% for 'Killarney' and 14% for 'Canby' red raspberry plants. The average maturity date for 'Prelude' is one to two weeks earlier than that of its parent 'Hilton'. While the parent of 'Prelude' NY817 was selected in 1964 and is now extinct, old field notes indicate its maturity date to be two to three weeks earlier than that of 'Prelude'.

Figure 4:
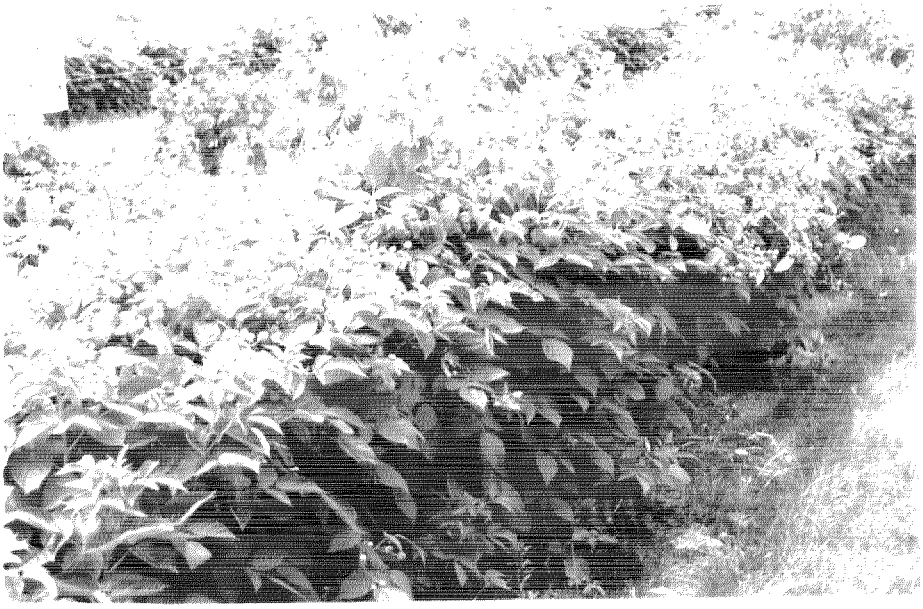
FIG. 4 is a photograph showing fruiting plant rows of 'Prelude' canes, with the fruit being on floricanes in summer.

FIG. 4 shows the vigorous nature of 'Prelude' red raspberry plants.

Figure 3:
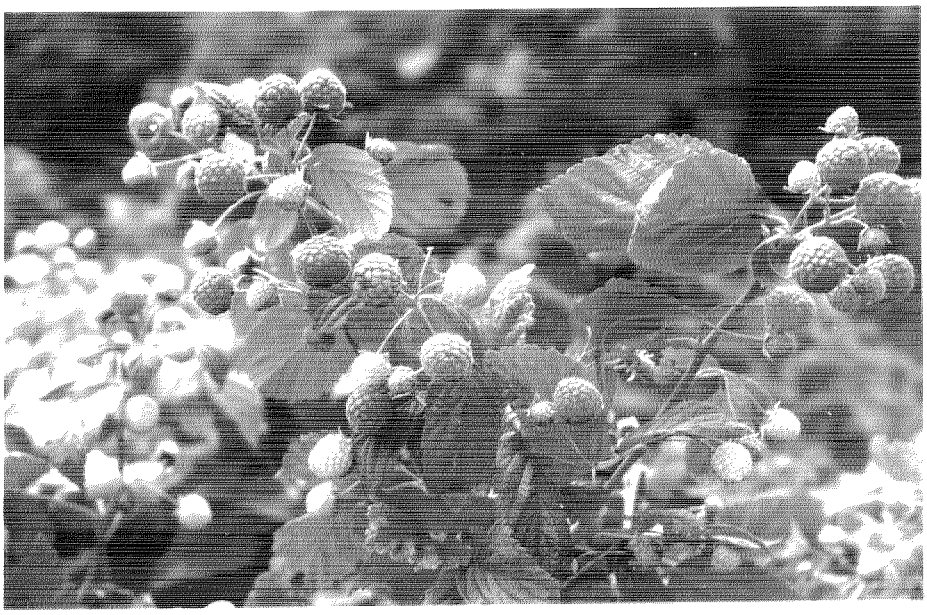
FIG. 3 is a photograph showing typical fruiting canes of 'Prelude' plants in the field, with the fruit being on floricanes in summer.

FIG. 3 shows typical fruiting floricanes of 'Prelude' red raspberry plants in the field in summer and shows open positioning and good placement of fruit.

Figure 6:
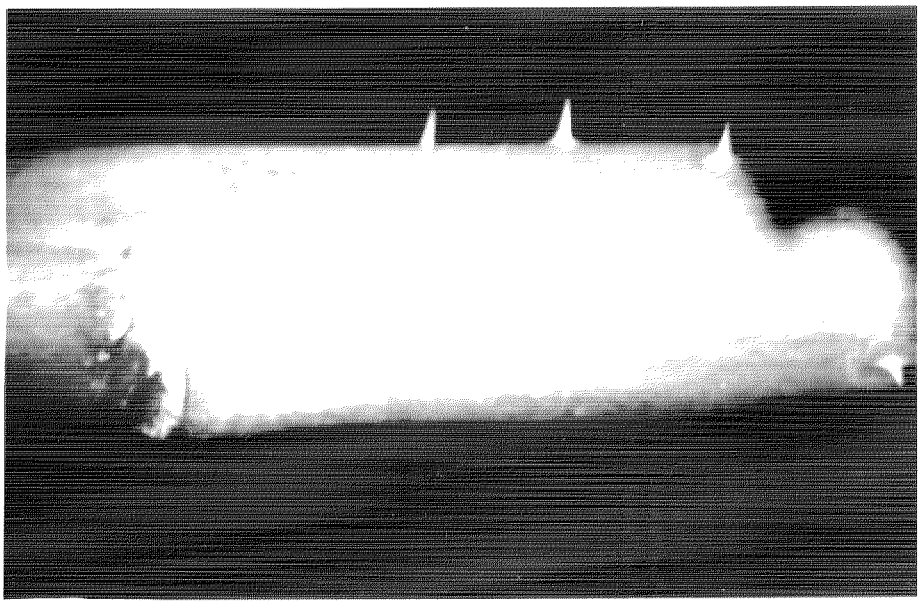
FIG. 6 is a photograph showing a dormant cane base of a 'Prelude' red raspberry plant.
Figure 7:
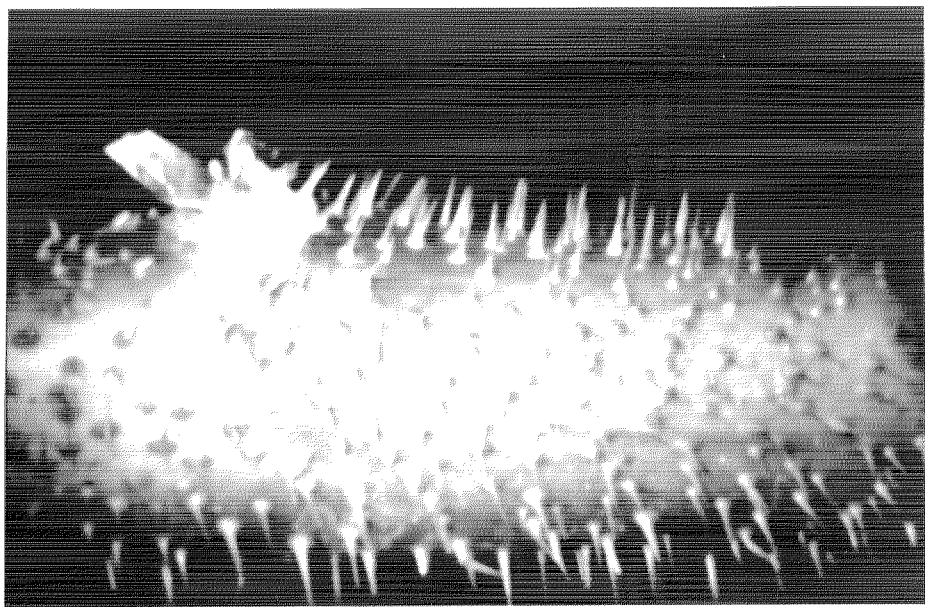
FIG. 7 is a photograph showing a dormant cane base of a 'Killarney' red raspberry plant.
Figure 11:
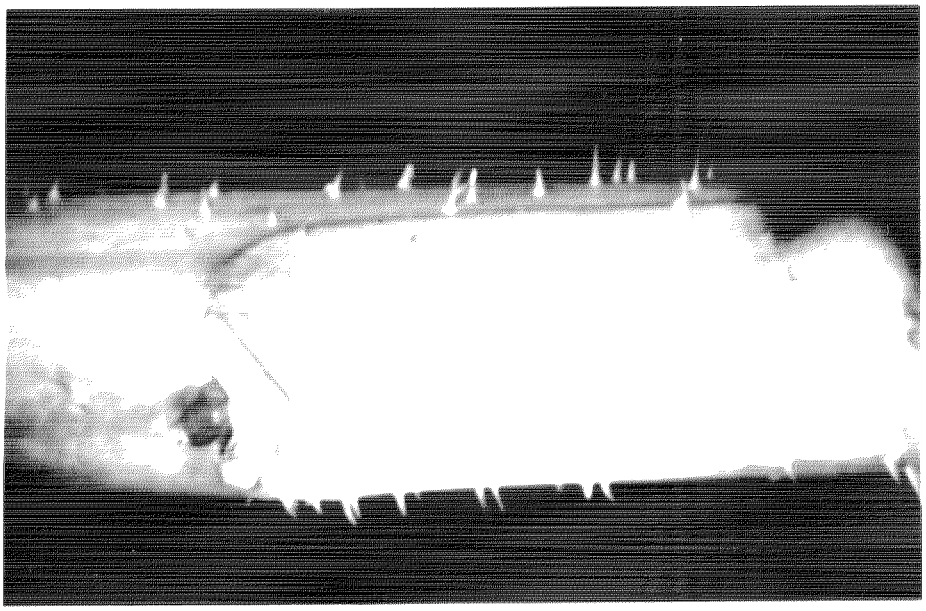
FIG. 11 is a photograph showing a dormant cane base of a 'Titan' red raspberry plant.

FIG. 6 shows a dormant cane base of a 'Prelude' red raspberry plant. As shown in FIG. 6, the dormant cane base has very few spines. The dormant cane base color as observed in the field is most similar to Greyed-Orange 165-Group C. This color code and the others hereinafter correspond to those in The Royal Horticultural Society Colour Chart, London. The density of the spines at the base of the canes of 'Prelude' is different from the density of the spines at the base of the canes of 'Titan' red raspberry plant (patented as N.Y. 883, U.S. Plant Pat. No. P.P. 5,404) and different from the density of the spines at the base of 'Killarney' red raspberry plant. The color of the cane base of 'Prelude' is different from the color of the cane base of 'Killarney'. FIG. 7 shows a dormant cane base of a 'Killarney' red raspberry plant. As shown in FIG. 7, the dormant cane base of 'Killarney' red raspberry plant has spines present in high density which are long in length and point downward. The dormant cane base color of 'Killarney' as observed in the field is similar to Greyed-Orange 166-Group A. FIG. 11 shows a dormant cane base of a 'Titan' red raspberry plant. As shown in FIG. 11, the dormant cane base of 'Titan' red raspberry plant has spines which are thin in shape, present in less density than the spines for 'Killarney' red raspberry plant and in greater density than the spines for 'Prelude' red raspberry plant. The dormant cane base color of 'Titan' as observed in the field is similar to Greyed-Orange 165-Group C.

Figure 8:
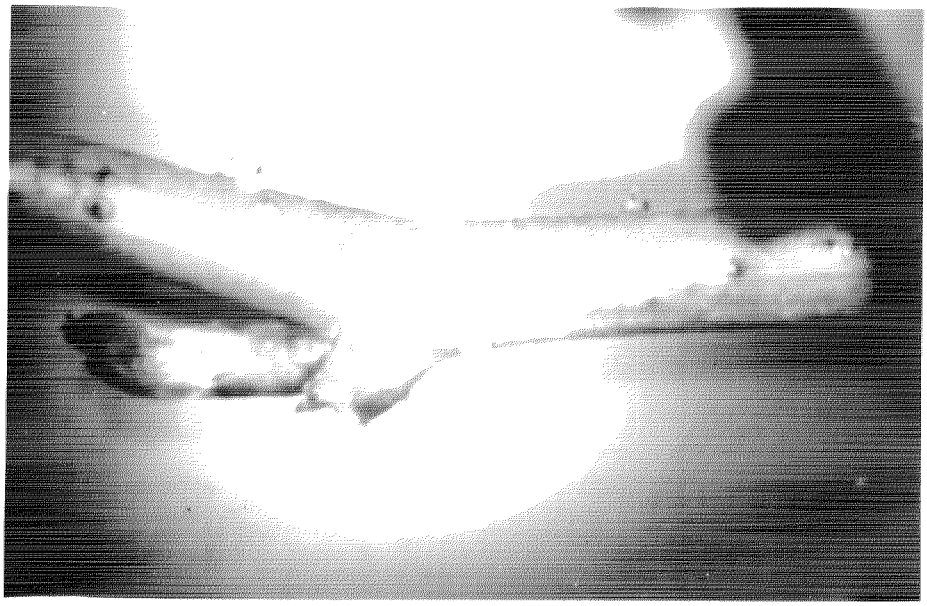
FIG. 8 is a photograph showing a dormant cane tip of a 'Prelude' red raspberry plant.
Figure 9:
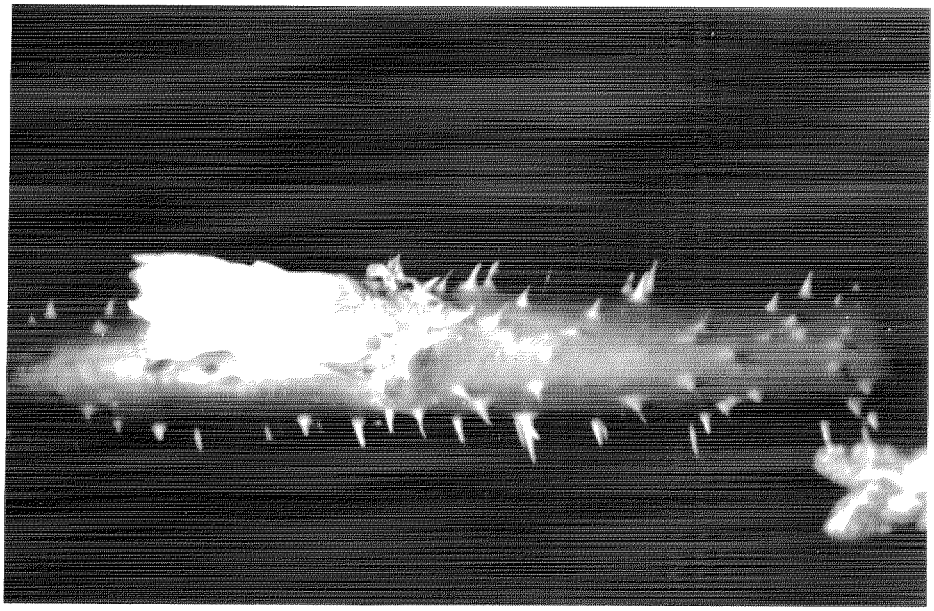
FIG. 9 is a photograph showing a dormant cane tip of a 'Killarney' red raspberry plant.

FIG. 8 shows a dormant cane tip of a 'Prelude' red raspberry plant. As shown in FIG. 8, the dormant cane tip has a sparse number of spines which have a wide diameter base. As shown in FIG. 8, leaf tissue emerging from buds has red pigmentation at the tip. The dormant cane tip color of 'Prelude' as observed in the field is similar to Greyed-Orange 164-Group A. FIG. 9 shows a dormant cane tip of a 'Killarney' red raspberry plant. As shown in FIG. 9, the dormant cane tip has long thin spines that point downward which are present in high density. The cane tip color of 'Killarney' as observed in the field is similar to Greyed-Purple 183-Group A.

Figure 10:
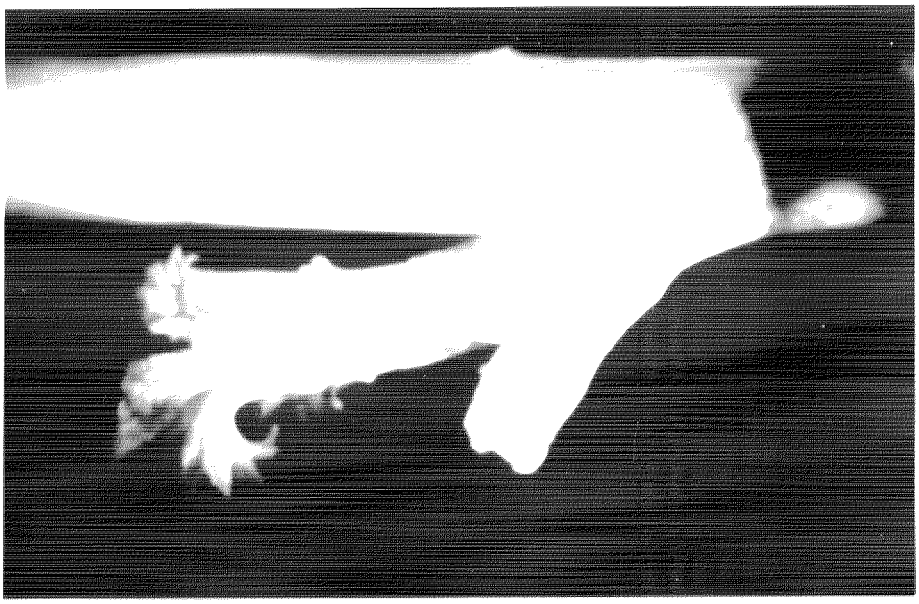
FIG. 10 is a photograph showing a 'Prelude' plant cane with leaf emergence buds.

FIG. 10 shows a cane of a 'Prelude' red raspberry plant, with leaf emergence from buds. Note the red pigment on the leaves.

While the observed colors may differ from those shown in FIGS. 6, 7, 8 and 11, THIS IS because FIGS. 6–11, as indicated above, were taken under magnification under artificaial lighting in a procedure ordinarily carried out under artificial lighting. In other words, the photographs of FIGS. 6–11 are anot ment to show color true to life as they are magnified and shown under artificial lighting but rather are to show spine density and spine detail differences. The magnification was necessary to show the spine detail and spine density differences which the photos are to illustrate. The photos are effective to show said spine detail and spine density differences and also the presence of differences in coloration between cultivars. The observed colors confirm the presence of differences in coloration shown in the photographs and indicate the specifics of the differences. So far as the recited observed colors are concerned, the color chart readings are the closest approximation to the mean color of each cultivar as the RHS color charts are not expansive enought to be exact. Mean color is referred to because there are color variations with each clone due to environmental factors such as age of the plant, temperature, and moisture levels that interact with the physiology of the plant.

We turn now to information on leaves of 'Prelude'. The leaf arrangement on 'Prelude' is compound with three leaflets. The rachis length averages 3 cm and the teriminal leaflet petiole averages2 cm. The lateral leaflets do not have petioles. There are two stipules present and the cross section of the leaf is concave. The terminal leaflet on 'Prelude' averaragesw 8 cm in length and 5 cm in width with no overlap in fully expanded mature leaves. The orientation is digitate. The leaflet shape is ovate with an acute tip and a rounded base. The shape of the margin is doubly serrate. The color of the terminal leaflets varies with age and health, but in fully expanded spring growth most resembles the Yellow-Green 144—Group B on the upper surface and the Yellow Green 144—Group A on the lower surface. The rachis and petiole color most resembles the Yellow-Green 144—Group A on the upper surface and the Yellow-Green 144–Group B on the lower surface. The lateral leaflets on 'Prelude' average 6 cm in length and 4 cm in width. There is no overlap in fully expanded leaves. The orientation is digitate. They are ovate in shape with an acute tip and a rounded base and a doubly serrate margin. The upper surface of fully expanded spring growth most resembles the Yellow-Green 144—Group A and the lower surface resembles the Yellow-Green 144—Group B althought the colors vary with the age and health of the leaves.

We turn now to the flowers on 'Prelude'. The flowers on 'Prelude' are rosaceous and are actinomorphic in shape with five elliptical shaped petals. They average 1 cm in diameter. Clusters average seven flowers with pedicels averaging 1.5 cm in length. The pedicel color most closely resembles the Yellow-Green 146—Group A with overtones of the Red47—Group A. The petal color most closely resembles the Yellow-White 158—Group D.

Figure 2:
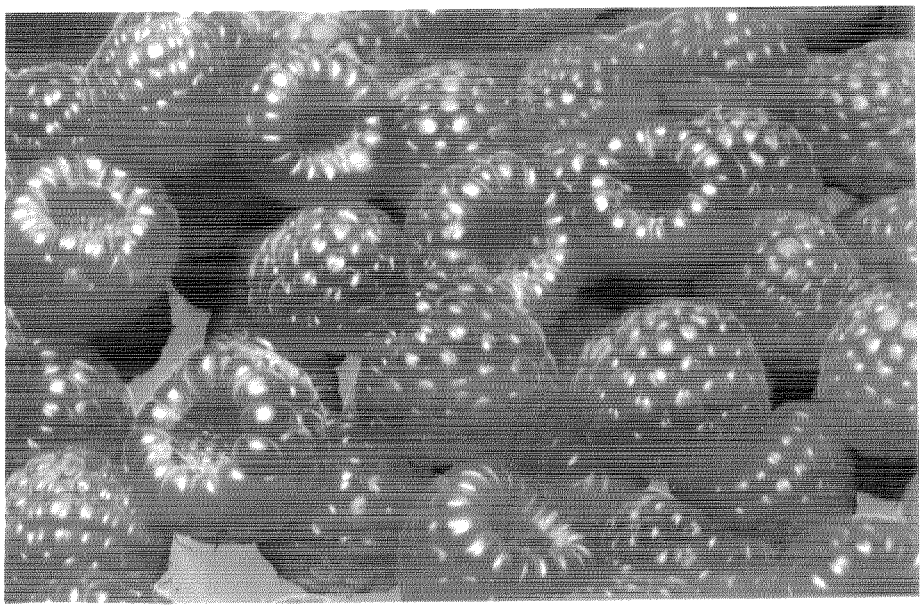
FIG. 2 is a photograph of 'Prelude' fruit which has been washed and photographed under bright light to show the fruit to best advantage for a publication.
Figure 5:
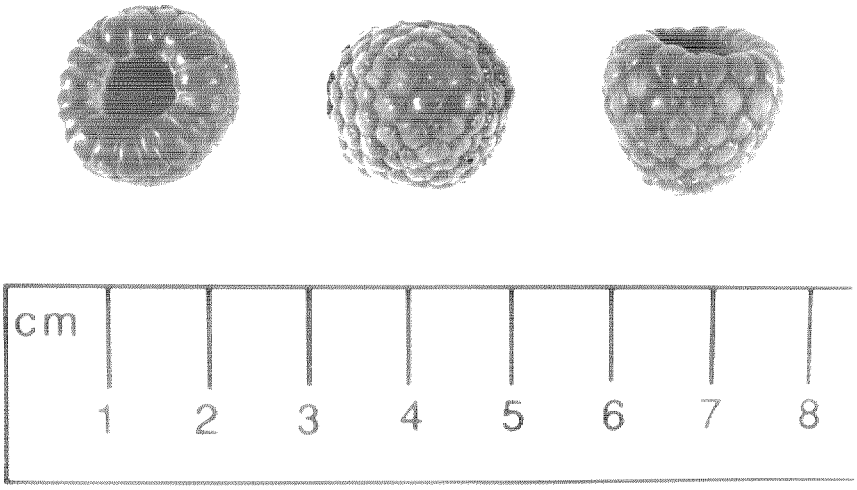
FIG. 5 is a photograph showing the size and true color of 'Prelude' fruit.

FIG. 2 shows uniformity of size and shape of fruit of a 'Prelude' red raspberry plant. The berries have strong coherence at the base. FIG. 5 shows true color and dimensions of a raspberry from a 'Prelude' red raspberry plant from three views. The true fruit color is most similar to Red 39—Group A.

Average fruit size and yield are similar to other early varieties. The fruit width of 'Prelude' averages 1.75 cm, and the fruit length of 'Prelude' averages 1.5 cm. The number of druplets averages 87 per fruit. The average fruit size of 'Prelude' is smaller than the average fruit size of 'Hilton', 'Prelude' fruit are firmer than the fruit of 'Reveille' and 'Lauren' (U.S. Plant Pat. No. 10,610).

'Prelude' berries separate from the torus more readily than berries of 'Hilton' making them easier to pick.

Table 1 below sets forth total fruit yield in kg/ha and average fruit size in grams for floricane yield at Darrow Farm, located on Gates Road in Geneva, N.Y., for 1995 and 1996 for 'Prelude,' 'Killarney,' 'Canby' cultivars and for an average of 11 other cultivars. The test trial was established in 1994, using a randomized complete block diagram. There were five replicates per cultivar. The data of Table 1 are the means of five replicates.

TABLE 1

| | Total fruit yield kg/ha | | | Average fruit size in grams | | |
|---|---|---|---|---|---|---|
| Cultivar | 1996 | 1997 | Average | 1996 | 1997 | Average |
| Killarney | 16,718 | 13,150 | 14,934 | 2.55 | 2.10 | 2.33 |
| Canby | 11,012 | 10,389 | 10,701 | 2.10 | 1.75 | 1.93 |
| Prelude | 5,452 | 11,048 | 8,250 | 2.40 | 2.00 | 2.20 |
| Average of 11 other cultivars | 8,565 | 8,562 | 8,564 | 2.83 | 2.39 | 2.56 |

Table 2 below sets forth the total fruit yield in kg/ha and an average fruit size in grams for floricane yield at Robbins Farm, located on Sutton road in Geneva, N.Y., for the years 1994–1997. This test trial was established in 1990. Data listed in the table are from individual plots unless denoted by parentheses, indicating the number of replicates analyzed per year. The data for 'Prelude' cultivar does not include fall-season yields.

TABLE 2

| Cultivar | 1994 | 1995 | 1996 | 1997 | 94–97 Average |
|---|---|---|---|---|---|
| | Average Fruit Size in Grams/Berry | | | | |
| Encore | 3.10(2) | 2.78(4) | 2.96(3) | 2.80(3) | 2.91 |
| Prelude | — | 2.02 | 2.28 | 2.43 | 2.24 |
| Killarney | — | 2:14 | 2.43 | 1.96 | 2.18 |
| Canby | — | 2.20(2) | 2.15 | 1.98 | 2.11 |
| Sentry (unpatented) | 2.31 | 2.18 | 2.13 | 1.93 | 2.14 |
| | Total Yield in kg/ha | | | | |
| Encore | 7,224(2) | 8,838(4) | 9,247(3) | 7,422(3) | 8,183 |
| Prelude | — | 7,812 | 7,995 | 7,728 | 7,845 |
| Killarney | — | 7,267 | 7,814 | 8,244 | 7,775 |
| Canby | — | 8,153(2) | 11,342 | 3,435 | 7,643 |
| Sentry (unpatented) | 4,110 | 4,675 | 7,796 | 2,369 | 4,738 |

'Encore' red raspberry plant referred to in Table 2 above and Tables 3 and 4 below is the subject of a pending U.S. plant patent application which has been assigned application Ser. No. 09/166,855.

'Prelude' red raspberry plant average fruit size from 1994 to 1997 was equal to that from 'Canby' and 'Killarney' cultivars at both the Darrow and Robbins trial locations (Tables 1 and 2, above).

'Prelude' red raspberry plant total summer fruit yield at the Robbins research farm from 1994 to 1997 was equal to that from 'Canby' and 'Killarney' cultivars (Table 2). 'Prelude' red raspberry plant total summer yield at the Darrow research farm was less than from 'Killarney' and 'Canby' cultivars but similar to the average yield of other cultivars in the trial.

Plant vigor and fruit production has not declined when summer cropping annually; fruit production for years 1995, 1996 and 1997 have been both consistent and substantial (Table 2).

'Prelude' red raspberry plants also bear fruit on primocanes in the fall. Results from test trials of primocane yield in the fall at Darrow research farm over the period 1995 to 1997 for 'Prelude' and four other cultivars are set forth in Table 3 below. This test trial was established in 1994 using a randomized complete block design. There were five replicates per cultivar. The data in Table 3 are means of five replicates. There are two entries for 'Prelude' cultivar in Table 3, namely "z" and "y." The "z" entry gives results when the plants were grown in an annual fall cropping system. The "y" entry gives results for fall production when the plants were double cropped, i.e., where floricanes were harvested the same season. The plots for the "y" entry tests were grown in an adjacent trial where typical cultural practices for summer fruit production were utilized. Red raspberry plants of parent 'Hilton' do not produce fruit on primocane growth.

'Prelude' averages eleven new primocanes per crown each year. The diameter of the primocanes at the base averages 1 cm and 0.75 cm at the middle third. The floricane diameter at the base averages 1.2 cm and 1 cm at the middle third. The primocanes average 130 cm in length. The floricanes average 150 cm in length. Primocane and floricane bud break/shoot emergence averages April 7 in Geneva, N.Y. The average internode distance is 3.75 cm for primocanes and 5.75 cm for floricanes.

The number of fruiting laterals on 'Prelude' averages 11 per cane on primocanes and 17 per cane on floricanes. 'Prelude' averages 9 nodes per fruiting lateral for floricanes with an average of 1.5 flowers per node.

We turn now to Table 3 which is referred to above:

TABLE 3

| | Total yield kg/ha | | | | Average fruit size in grams | | | |
|---|---|---|---|---|---|---|---|---|
| Cultivar | 1995 | 1996 | 1997 | Average | 1995 | 1996 | 1997 | Average |
| Autumn Bliss* | 3,118 | 6,624 | 9,197 | 6,313 | 1.6 | 2.6 | 2.2 | 2.2 |
| Ruby | 4,890 | 3,695 | 4,304 | 4,284 | 1.9 | 2.1 | 2.2 | 2.1 |
| Heritage | 4,495 | 3,997 | 3,951 | 4,147 | 1.5 | 1.4 | 1.5 | 1.5 |
| Amity | 2,653 | 2,659 | 5,286 | 3,532 | 1.6 | 1.9 | 1.7 | 1.7 |
| Prelude[z] | 4,426 | 4,696 | 4,044 | 3,389 | 1.7 | 1.8 | 1.8 | 1.8 |
| Prelude[y] | — | 1,353 | 1,382 | 1,368 | — | 1.7 | 1.9 | 1.8 |

Ruby™, referred to in Table 3 above, is the trademark associated with the cultivar 'Watson' which has been patented in the United States (U.S. Plant Pat. No. 7,067).

When 'Prelude' red raspberry plants were double cropped (harvesting both the summer and fall crop in the same year), the combined yields were above average (Tables 1 and 3), reflecting higher total yield potential.

'Prelude' red raspberry plants perform well when grown under an annual production system, harvesting the fall crop only. In comparison to Heritage, 'Prelude' produces lower fruit yields but larger average fruit size (Table 3). The fall season maturity of 'Prelude' is generally the same as Heritage.

The fruit of 'Prelude' red raspberry plants has a mild and pleasant flavor.

Juice soluble solids (sugars), total acidity and pH values for 'Prelude,' 'Canby' and 'Killarney' cultivars and an average of other cultivars are set forth in Table 4, below. Average soluble solids, total acidity and pH values in Table 4 are from the average of the three years, 1995 to 1997, and minimum and maximum scores are for the total period and are not averages. In Table 4, the superscript "z" indicates the mean of 25 other cultivars tested from 1995 to 1997 and the superscript "y" indicates the mean of 13 other cultivars tested from 1995 to 1997. In Table 4, "Ave." means average, "Min.," means minimum, and "Max." means maximum.

TABLE 4

| | Soluble Solids (°Brix) | | | Total Acidity | | | pH | | |
|---|---|---|---|---|---|---|---|---|---|
| Cultivar | Ave. | Min. | Max. | Ave. | Min. | Max. | Ave. | Min. | Max. |
| Prelude | 10.6 | 9.0 | 11.6 | 1.54 | 1.49 | 1.59 | 3.28 | 3.25 | 3.30 |
| Canby | 11.5 | 10.1 | 13.8 | 1.38 | 1.09 | 1.75 | 3.28 | 3.10 | 3.40 |
| Killarney | 9.4 | 9.0 | 12.2 | 2.12 | 1.92 | 2.43 | 3.12 | 3.00 | 3.20 |
| All Others | 10.1[z] | 7.2 | 14.4 | 1.94[y] | 1.49 | 2.43 | 3.19[y] | 2.85 | 3.70 |

As indicated in Table 4, "juice soluble solids" for 'Prelude' cultivar is above average and "total acidity" is below average.

Acceptable fruit quality was maintained in storage tests at 0° to 1° C. for two to three days.

Alternate year mowing may be a useful cultural practice for 'Prelude' red raspberry plants, reducing the amount of hand-pruning, while still harvesting three crops (fall, summer, fall), every two year.

Dormant pruning is essential for maintaining proper cane densities for fruit production. When dormant pruning, it is important to cut back the tip of the canes to just below the last node which produced flowers the previous fall.

Trellis support is not required since canes are sturdy and are able to support and display ripe fruit without sprawling.

It is beneficial to remove fruiting canes in the summer if it is planned to harvest fruit again from the primocanes in the fall.

When double-cropping, it is essential to maintain a fertilizer program for both the summer and fall crops.

The grower has the following options.

The growers can use cultural practices aimed at maximizing the summer crop.

Alternatively, the grower can mow off canes in the dormant season and just harvest the fall crop.

Alternatively, the grower can prune normally, and maximize yields by harvesting both summer and fall crops.

'Prelude' red raspberry plants have not been noted to be particularly resistant or susceptible to any raspberry pests in the Northeast region.

What is claimed is:

1. A new and distinct raspberry plant, 'Prelude' as herein described and illustrated and identified by the characteristics enumerated above.

* * * * *